United States Patent [19]

Hunter et al.

[11] 4,163,643

[45] Aug. 7, 1979

[54] AUTOMATION OF DISCRETE ANALYSIS SYSTEMS

[75] Inventors: William M. Hunter; John D. Lock, both of Edinburgh, Scotland

[73] Assignee: National Research Development Corporation, London, England

[21] Appl. No.: 855,768

[22] Filed: Nov. 29, 1977

[30] Foreign Application Priority Data

Dec. 3, 1976 [GB] United Kingdom ............... 50517/76

[51] Int. Cl.² .............................................. G01N 1/10
[52] U.S. Cl. .................................. 23/230 R; 366/109; 422/65
[58] Field of Search ................. 23/259, 253 R, 230 R; 366/111, 109, 114; 233/3, 5

[56] References Cited
U.S. PATENT DOCUMENTS

| 2,916,266 | 12/1959 | Pray | 366/109 |
| 2,978,231 | 4/1961 | Eisenberg | 366/109 |
| 3,289,610 | 12/1966 | Lounsbury et al. | 366/109 |
| 3,576,313 | 2/1969 | Derderian | 366/109 |
| 3,617,222 | 11/1971 | Matte | 23/230 R |
| 3,876,379 | 4/1975 | Ghim | 23/259 |
| 4,007,011 | 2/1977 | Greaves et al. | 23/259 |

Primary Examiner—R. E. Serwin
Attorney, Agent, or Firm—Oblon, Fisher, Spivak, McClelland & Maier

[57] ABSTRACT

The invention concerns the use, in discrete sample analysis apparatus, of vibratory conveyor to convey samples, and there is provided an automated discrete analysis system in which the means for conveying samples through the system comprises vibratory conveyor. A particular example described in detail is that of an automated radioimmunoassay system which in preferred form consists of a series of linked spiral vibratory conveyor modules.

23 Claims, 10 Drawing Figures

AUTOMATION OF DISCRETE ANALYSIS SYSTEMS

This invention relates to the automation of discrete analysis systems and in particular to the automation of binding assay techniques such as Radioimmunoassay (RIA), and immunometric assay techniques.

Many of the routine analytical techniques customarily employed in clinical and other laboratories have now been automated to alleviate tedium and release skilled technicians for other tasks. Generally these automated systems fall into two main categories, either continuous flow or discrete sample systems, and this invention relates to apparatus of the latter type.

In recent years RIA and other binding assay techniques have become immensely important for determination of biologically active materials, many of which cannot be assayed by other techniques, and there is a growing demand for a cheap reliable automated RIA system. These techniques, however, involve procedures which are not inherently suited to automation, and most available systems are either highly complex and thus expensive or represent only partial automation and require manual intervention at many stages. In particular these techniques characteristically involve incubation of an antigen or a hapten with an antiserum and, in the case of RIA, radioactive counting, both of which may require widely varying periods of time dependent upon the nature of the assay being performed. For example, the period required for incubation may vary from about fifteen minutes up to about thirty-two hours and for radioactive counting from about ten seconds up to about four minutes. Such breadth of variation cannot easily be accommodated by conventional automated discrete analysis systems such as the continuous belt mechanisms previously used. A simple automated system has now been devised which permits great flexibility of sample throughput and is particularly applicable to the automation of binding assay techniques.

Accordingly the present invention comprises an automated discrete analysis system in which the means for conveying samples through the systems comprises vibratory conveyor. In general, the invention includes the use, in automated discrete analysis systems, of vibratory conveyor to convey discrete samples.

The invention may be applied generally to the automation of assay systems based on the discrete sample principle, and is particularly applicable to those systems requiring flexibility of sample throughput. Advantageously the invention may be applied to the automation of binding assay techniques, and, without prejudice to the broader application, the present description concentrates upon this aspect. For example, the present invention may be applied to the automation of binding assay techniques such as protein binding assays, radio receptor assays and especially radioimmunoassays, and the automation of immunometric assay techniques, such as sandwich assays.

The vibratory conveyor of the present invention typically consists of a support for sample containers arranged to be vibrated in such a manner as to cause the containers to be transported along the support, and may include those types of vibratory conveyor which have been known or used previously.

The support may be in any suitable form, such as a trough or the like, for instance to accommodate the sample containers, usually cylindrical tubes, in an upright orientation. A preferred support for use in assay systems is a track comprising pairs of spaced apart parallel elongate members between which sample containers can hang freely supported by the members, for instance by means of an enlarged collar around the top of each tube which rests on the upper surfaces of the members. The track may be in straight sections as an "in-line" type conveyor and also in arcuate sections as a "spiral, helix or bowl" type conveyor.

The support or track is connected to a firm base by resilient mountings such as leaf springs and is provided with an appropriate vibrating means to vibrate the support, usually in a combined up-and-down and to-and-fro motion. The vibrations may be supplied mechanically, for instance by a crank or the like or alternatively by rotation of eccentrically mounted masses. Preferably, however, the vibration is supplied electrically, for instance piezoelectrically by excitation of piezoelectric crystals attached to the leaf springs which carry the support or electromagentically by excitation of the support relative to the base. In particular it has been found that the oscillating frequency of the mains supply (50 cycles per second) may be used advantageously to provide a very simple and reliable means for vibrating the track. The vertical and horizontal components of the vibration may be provided separately if desired, for instance to exercise a greater degree of control over the conveyor.

The sample containers may be introduced to the support by means of an automatic feeder system, and in a preferred embodiment a vibratory bowl feeder is employed. Such an automatic feeder may be used to place the sample tubes in the correct orientation for introduction to the track, may also conveniently incorporate a facility for recognising and rejecting mis-shapen or otherwise unsuitable tubes which could jam in subsequent components and advantageously obviates the need, present in previous systems, for the conveyor to be loaded manually. Generally also tedious sample identification procedures may be alleviated by use of suitable labelling techniques. For example, the sample containers which are loaded into the vibratory feeder may be labelled with a suitable code such as a bar-code and the feeder may be used in combination with an appropriate code reader. In addition when samples are transferred from one container to another during the assay procedure, both containers may be labelled with suitable codes and the system may be provided with means for identifying and equating or transferring these codes from one tube to another.

The automated binding assay systems of the present invention are usually modular in construction and vibratory track conveyor of the "in-line" type may be conveniently employed in some cases to convey the sample containers from one module to another. Generally the track is supplied with suitable gate mechanisms at appropriate points along its length by means of which movement of the sample containers along the track may be arrested to allow for time lapses required by the assay technique e.g. for incubation and radioactive counting, and for this purpose geneva type gate mechanisms have been found to be highly satisfactory. A preferred gate mechanism for use in the apparatus of invention consists of a lever mechanism providing combined barrier and clamping means which either bar passage of a queue of sample containers, or, on actuation, act to clamp the second or subsequent container in the queue whilst releasing the first container or containers to proceed along the conveyor. In one form, this preferred mechanism comprises parallel elongate barrier and clamping members disposed across the conveyor track and separated from one another by a transverse interconnecting member which is pivoted about an axis parallel to the barrier and clamping members and pivotable by means of an actuator such as solenoid or piston actuator. In the normal rest position the barrier lays across the conveyor providing a barrier behind which sample containers queue; actuation of the mechanism raises the barrier to release the first container whilst bringing the clamping member to bear on the second or a subsequent container and maintain the queue, and on return of the mechanism to the rest position the queue of containers moves forward to take up station at the barrier. The preferred gate mechanisms per se are included within the scope of the invention.

Preferably the track is provided in an appropriate form to accommodate an extensive number of sample containers, for instance whilst queuing during the incubation period or prior to counting e.g. radioactive counting. In a particularly preferred embodiment vibratory track conveyor of the "spiral" type is employed to provide a queuing zone for sample containers, and if it is desired to increase the capacity of this queuing zone a plurality of linked spirals may be employed. For example, spirals may be interconnected by "in-line" type conveyor, or preferably may be stacked one on top of another with adjacent spirals mutually reversed, for instance with the innermost turn of the upper spiral formed into a down going ramp which is continuous with the innermost turn of the reversed spiral below. In this way sample containers may be allowed to enter the upper spiral at its periphery travelling inwards towards its centre, then downwards into the reverse spiral and finally return for exit at the periphery below without recourse to any mechanism other than vibratory force. It will be apparent, however, that other means may be employed to transfer sample containers from one spiral to another.

The above preferred embodiment provides a basic unit from which the overall discrete analysis system may be constructed, optionally together with "in-line" type conveyor to connect the various spiral units. For example, spiral units, whether constructed from a single spiral or plurality of spirals, may provide separate queuing zones during primary, secondary and further incubations, and also prior to introduction of samples to an appropriate counting system e.g. radioactive counter. Conveniently these spiral units may be simply and cheaply constructed from a few standard components which may, for instance, be moulded or cast from a suitable material such as a synthetic plastic e.g. PVC. In addition, the spiral unit of the preferred embodiment may be removed from the on-line system for off-line processing and advantageously may satisfy a "cassette"-like function; for instance for storage of samples e.g. under refrigeration, prior to introduction to the system, or for incubations which require particularly extended periods of time.

The present invention is advantageously applicable to binding assays in which solid phase first antibody or solid phase second antibody (DASP) techniques are employed to separate bound and free labelled antigen or antibody. Conveniently the vibratory motion of the conveyor may be used to agitate the solutions and/or hold solid phase material e.g. solid phase antibody reagent, in suspension during incubation. In such cases also it may be desirable to separate the horizontal and vertical components of the vibratory force, for instance as described in U.K. Pat. No. 1,154,042. Thus, for example, a spiral track vibratory conveyor having a ridged rubber floor may be employed and the amplitude of the vertical component varied; low amplitude vibrating the sample containers against the ridges and agitating the solutions, or high amplitude causing the containers to surmount the ridges and so progress around the spiral track.

A preferred agitator which also relies upon the vibratory motion of the conveyor has been devised essentially comprising vibratory track conveyor so oriented that sample containers rest on their sides at an angle out of the vertical. It has been found that sample containers, when queued in such a length of vibratory track conveyor, execute a gentle rolling motion which advantageously mixes their contents. The length of vibratory track conveyor typically comprises a gate mechanism towards the exit end to provide for the required queue of containers. In a preferred container design the mixing affect may be further enhanced by including webs or baffles down the inside walls of the container. Preferably the containers rest at an angle of up to about 50° from the horizontal, especially about 40° from the horizontal. The preferred agitator may be provided as a length of "in-line" conveyor, or more preferably within a spiral unit, for instance, as an inclined circuit around the periphery of a spiral unit. It will be appreciated, however, that agitators employing the vibratory principle described above have more general application than the vibratory conveyor systems of the invention, and such more generalised agitators are included within the scope of the invention. Such agitators typically comprise a support for containers, so arranged that containers rest on their sides at an angle out of the vertical on the support, and a means for supplying vibratory motion to the support such that the sample containers execute a gentle rolling motion and thereby mix their contents.

Vibratory track conveyor may also be used in separation modules for separation of solid phase binding reagent after incubation such as the separation apparatus described in our previous U.K. application No. 47078/75. In such separation modules the sample tubes generally hang freely in a vertical orientation in the conveyor track, and it has been found surprisingly that the vibratory motion required to conveyor the containers does not substantially hinder the settling of the solid phase binding reagent. Preferred separation modules comprising vibratory conveyor are those based on the separation method described in our previous U.K. patent application No. 47078/75 in which solid phase binding reagent is separated from suspension by addition of a second liquid having a density intermediate between those of the solid and liquid components of the suspension, to form, above or below the suspension, a discrete layer into which the solid binding reagent separates. Such preferred separation modules comprise vibratory conveyor, preferably spiral conveyor, typically in combination with a gated station for addition of the second liquid and may also include a second gated station for removal of supernatant liquid as well as further stations for addition of further "intermediate density" liquids of progressively greater density and removal of supernatants.

Counter-Detector modules, such as radioactive counting modules, may also comprise vibratory conveyor, preferably spiral type conveyor to advantageously provide a holding zone for sample tubes prior to counting. Such modules are typically provided with a gated station towards the exit end for interaction with an appropriate detector e.g. $\gamma$-counter, liquid scintillation counter, spectrophotometer or fluorimeter, and the station and counter may be replicated in series as desired. For example a $\gamma$-counter may take the form of a well-type counter which rises from below to enclose the gated container during the counting sequence.

Vibratory conveyor is preferably also employed in the sampler and dilution module. For instance sample containers are stored in a spiral unit of the preferred embodiment from whence they are presented to a sampling station for transfer of an aliquot of sample to an empty sample tube, after which the initial sample containers may be returned to the top of the spiral unit or to a further spiral unit for storing. This sampler module and other modules comprising vibratory conveyor, such as the agitation module, the separation module and the radioactive or other counting module, are novel and are included per se or in any combination, as desired, within the present invention.

The apparatus of the invention may also, however, include modules similar to those used previously in prior art automated assay systems such as sampler and dilution modules based on the continuous belt principle.

In a particularly preferred embodiment vibratory conveyor is used throughout the discrete analysis system, especially in the form of preferred spiral units linked together. Conveniently the separate spiral units may be stacked one on top of the other to provide an overall system which is advantageously compact. For instance, a RIA system according to the invention may be made up of the various preferred modules described previously linked together and stacked one on top of the other, and is typically also provided with various gated stations at appropriate points for addition of reagents as desired such as antibody and labelled antigen solutions and solid phase antibody reagents. Such a stack of spiral units may be vibrated as a whole, for instance from an electromagnetic or piezoelectric drive acting on the bottom spiral of the stack which is rigidly connected to those above. More preferably, however the stack of spiral units are vibrated independently and each is freely located by resilient mountings e.g. leaf springs, within a rigid frame work.

Generally the automated systems described above are used in conjunction with suitable electronic processing equipment which operates the gate mechanism and sample delivery and removal sequences as desired, and may be conveniently programmed to satisfy the differing requirements of various assays.

In comparison with previously available discrete analysis systems, such as those employing endless belt mechanisms, the present system is typically a fixed system and only oscillates about a mean position. Thus, advantageously there is no requirement to link the input and output ends of the track, which removes a geometrical constraint normally present in discrete analysis systems. In addition the present system may conveniently accommodate, at a given time, different sample batches from unrelated assays having different time requirements e.g. for incubation, progress of samples through the system being determined by the period of operation of the gate mechanisms not the speed of the conveyor. Generally the system employs few moving parts, its mechanically simple and thus requires little maintenance.

This invention is further illustrated in the following description which refers to the accompanying diagrams in which.

Figure 1:
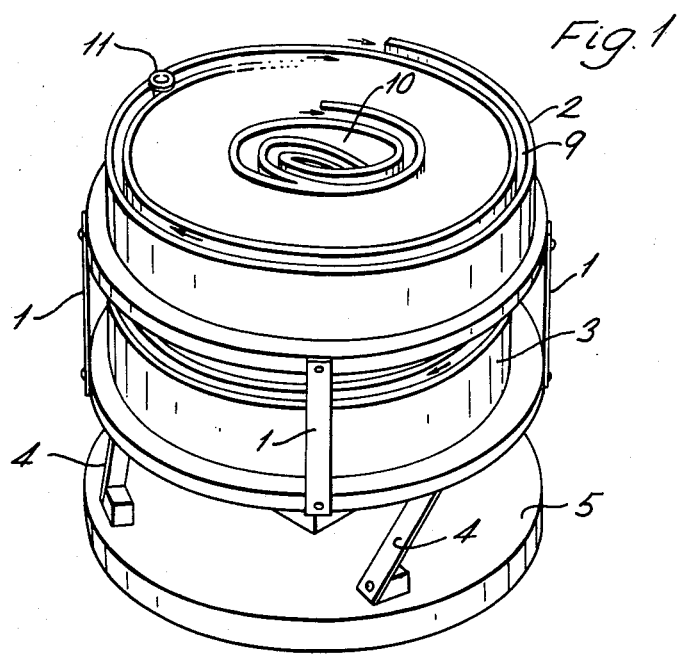
FIG. 1 is a side view from above of a standard double spiral vibratory track conveyor module as used in the discrete analysis system of the present invention.
Figure 2:
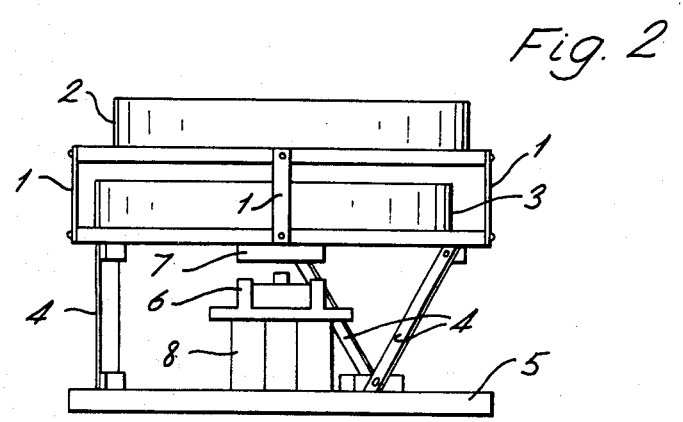
FIG. 2 is a side elevation of the module of FIG. 1.

FIGS. 1 and 2 represent the standard vibratory module which comprises two spiral vibratory track conveyors 2 and 3 located one above another, and held apart by vertical members 1. The lower vibratory spiral track 3 is supported by three inclined leaf springs 4, which are attached at their lower ends to a firm heavy circular base plate 5. Both spirals 2 and 3 are provided with a circularly oscillating vibratory motion by means of an electromagnet 6 mounted on pillars 8 which are fixed to the base plate 5, and a soft iron block 7 mounted on the base of the lower spiral track 3. The electromagnet 6 is energised by an oscillating current (e.g. oscillating mains frequency at 50 cycles per second) and in cooperation with the soft iron block 7 causes a vertical excitation force to be transmitted to the tracks 2 and 3, which due to the constraint of the leaf springs 4, results in an oscillatory motion consisting of two component vectors, one along the vertical axis and the other a torsional oscillation about the vertical axis. Double spiral modules suitable for use in automated assay systems, such as radioimmunoassay systems, preferably have a storage capacity of the order of about 640 tubes.

FIG. 1 shows a module having a clockwise upper spiral 2; though, in general, the standard module may be assembled with an upper spiral 2 which may be either clockwise or anti-clockwise depending upon its application. The spiral track 9 of the upper spiral 2 leads from its circumference to terminate at a convenient radius from the centre. Generally, also, the direction of inclination of the leaf spring 4 depends upon whether the upper spiral 2 is clockwise or anti-clockwise; though the inclination of the springs is usually such that sample tubes 11 are forced to move towards the centre of the upper spiral 2. The lower spiral 3 has a track which is the "mirror image" of the upper spiral 2, so that for a given leaf spring bias, the sample tubes 11 move towards the circumference of the lower spiral 3. From the inner radius of the spiral 2, the sample tubes 11 are conveyed downwards, the innermost turn 10 of the upper spiral 2 formed into a down-going ramp which is continuous with the innermost turn of the lower spiral 3. It will be appreciated, however, that any other suitable means may be employed to convey sample tubes 11 from the upper spiral 2 to the lower spiral 3.

In a further modification a plurality of pairs of spirals, similar to those shown in FIG. 1, may be stacked on top of each other, with ramps around their outer circumference to convey sample tubes from one pair of spirals to another. The stack is driven by a single drive at the base of the pile, and the whole arrangement being particularly desirable from the point of view of saving laboratory space.

Figure 3:
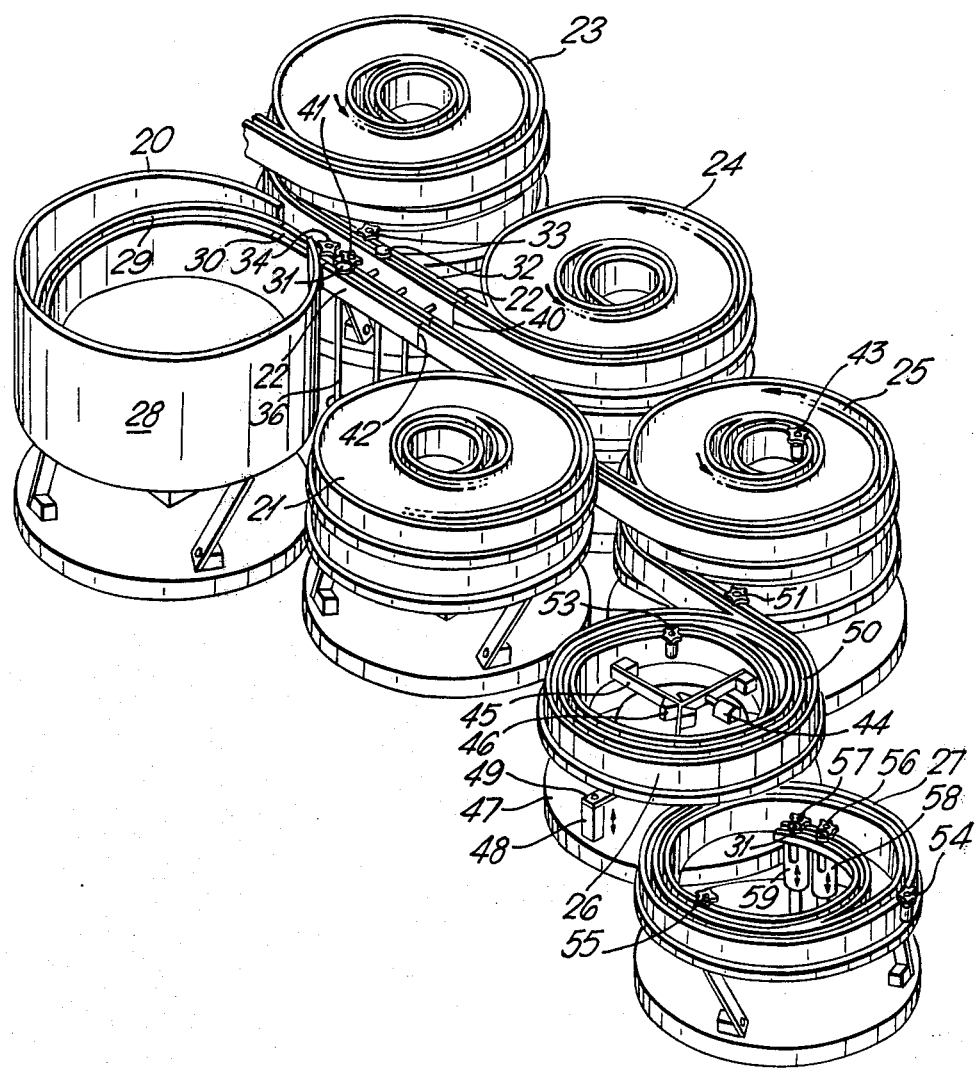
FIG. 3 is a view from above of an automated radioimmunoassay (RIA) system according to the present invention.

FIG. 3 represents an automated radioimmunoassay (RIA) system according to the present invention which is modular in construction and comprises a vibratory bowl feeder 20 linked to a primary incubation module 21 by a length of straight track 22. Track 22 also links a sample store 23 and a sample receiver 24. A further secondary incubation takes place in module 25 which is linked to module 21. The output of module 25 is fed to a final incubation module 26, and thereafter is a settling module 27 which combines separation and radioactive counting.

The vibratory bowl feeder 20 comprises a vertical-walled, circular bowl 28 and is located and supplied with oscillatory motion in a similar fashion as for the standard vibratory module illustrated in FIGS. 1 and 2. The bowl contains loops of conveyor track 29, rising in a spiral from the bottom of the feeder 20, exiting therefrom through an aperture 30 provided in its vertical wall, and connecting with the end of the straight track 22.

Figure 4:
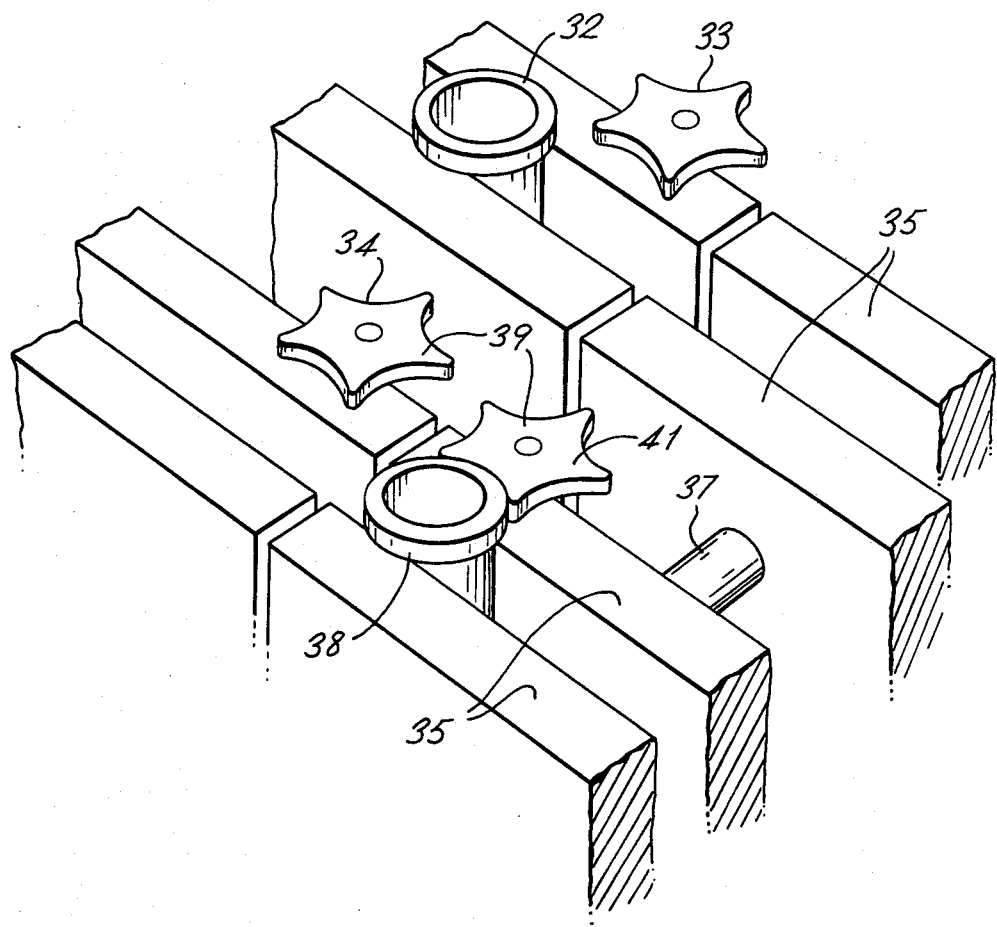
FIG. 4 is an enlarged view of the sampler station at the entry to the RIA system of FIG. 3.

FIG. 4 is an enlarged view of the entry to track 22.

The vibratory bowl feeder 20 is used to feed empty sample tubes 31 automatically into the system. For example, the empty tubes 31 are poured into the centre of the bowl 28 and the vibratory motion causes the tubes 31 to enter the bottom end of the track 29. Orientation devices (not shown) at the exit from the bowl 28 causes the tubes 31 to take up the correct vertical orientation before being fed to the beginning of track 22. The bowl feeder 20 conveniently includes a facility (not shown) for recognising and rejecting mis-shaped tubes which may jam in subsequent components.

The sample store module 23 is of the standard vibratory type, as described previously with reference to FIGS. 1 and 2, and is filled with tubes 32 containing samples e.g. plasma samples to be tested. These tubes 32 are previously spun in a centrifuge to separate the plasma, and are labelled with a suitable bar code to identify the patient and the assay type which is to be undertaken. These tubes 32 are fed from module 23 until they reach the geneva mechanism 33 at the interface between module 23 and track 22. At the same time, empty tubes 31 from the bowl feeder 20 are fed out of the bowl until they reach the geneva mechanism 34 at the interface between the bowl feeder 20 and track 22. The straight track 22 comprises two sets of parallel paths made up of parallel elongated members 35 supported on rigid pillars 36 and held together by dowels 37. The tubes 31 and 32 hang freely in the spaces provided between the elongated members 35, and have enlarged collars 38 around their top ends which rest on the upper surfaces of the elongated members 35.

The geneva type mechanisms used throughout the system e.g. 33 and 34, are conveniently electrically operated and have five toothed star wheels 39 which engage with the tops 38 of the tubes 31 and 32 and on turning through one position allow a single sample tube 31 to pass at predetermined intervals. An appropriately programmed electronic switching device (not shown) is used to energise the geneva gate mechanisms as and when desired. The gate mechanisms, 33, 34 serve to arrest the tubes 32 containing the plasma samples from module 23 and the empty tubes 31 from the bowl feeder 20 respectively for transfer of measured aliquots of standard and unknown solutions to the empty tubes 31.

The empty tubes 31 from the bowl feeder 20 have a sensitive jacket around the outside, (e.g. either UV sensitive or infra-red sensitive), so that the bar code can be read from the sampler module tubes 32 and transferred to the empty tubes 31. By this means tubes 31 which have been fed from the bowl feeder 20 carry a bar code, containing the patient and test information, further through the system.

After the sample transfer has been made, it is desirable to retain the bulk blood samples, and the geneva mechanism 33 pushes the tubes 32 along track 22 until they reach the interface 40 between track 22 and the sample retaining module 24. The geneva 33 provides sufficient force to transfer tubes 32 provided the length of track 22 is not excessive. Tubes 32 stack up along the length of track 22 until the geneva attempts to push an extra tube 32 into this length and hence transmits the push to the tube 32 at the end of the stack, and forces it across interface 40 where it is picked up by the vibrating force at the entry to module 24. Module 23 may be overfilled with a number of empty tubes to avoid leaving any sample tubes 32 containing serum on track 22 at the end of the assay. The sample tubes 32 are fed into module 24 as the assay progresses until at the end of the assay all the residual serum samples are retained in module 24.

A similar arrangement is provided for the tubes 31 containing aliquots of sample. After the aliquots have been transferred to the tubes 31 the geneva 34 indexes and passes the tubes 31 into the next geneva 41 at the start of track 22. At this station a measured amount of antibody (Ab) is added, and geneva 41 indexes to push the samples along track 22 until they reach interface 42 between track 22 and module 21. The bowl feeder 20 contains an excess of empty tubes and indexing of geneva 41 continues for a fixed number of times, after the last patient's blood transfer has been made, to ensure that the last aliquot of a particular assay has entered module 21. This is accomplished electronically by use of a shift register.

The tubes 31 are fed into module 21 at a rate which depends upon the radioactive counting time (every 15 seconds, for example). The storage capacity required between the antibody (Ab) addition at geneva 41 and the addition of the labelled antigen (*Ag) at geneva 43 depends upon the count time (which in turn dictates the rate at which tubes pass through the system) and the time of the primary incubation. If the time of the primary incubation (i.e. time delay between Ab addition and *Ag addition) is say two hours, then the required storage capacity is two hours ÷ 15 sec. = 480. The storage capacity can be increased as required for any range of assays by simply adding further modules like module 21, FIG. 3 showing a primary incubation storage capacity of approximately 960 tubes, consisting of one double spiral track 21 and one single spiral track (the upper ingoing portion of module 25). After a tube 31 enters module 21 it passes through this module until it reaches the geneva 43 where it waits. The electronic programming is so arranged that the desired incubation time elapses between the Ab addition and the *Ag addition. While this delay is taking place, a large number of tubes 31 are moving through module 21, and a queue of tubes 31 will develop at geneva 43. After the required delay time the *Ag additions are made (again in phase with the radioactive counter). Similarly time delay is provided between the *Ag addition and the DASP (solid-phase second antibody) addition, depending upon the secondary incubation time, and the secondary incubation storage capacity is determined in the same way as the primary incubation capacity.

With reference to FIG. 3, the DASP agitation module 26 vibrates separately in both torsional and vertical modes. The torsional vibration is provided by an electronic vibrator 44 which operates against one of the three radial leaf springs 45 on which the module 26 is supported. The inner ends of these leaf springs 45 are held securely at the centre of a circular plate 46 which in turn is supported on a heavy base plate 47 by way of three rigid vertical pillars 48 and three horizontal leaf springs 49. The circular plate 46 is provided with vertical vibrations by means of an electromagnet and soft iron block device as in FIGS. 1 and 2. In this manner the track 50 of module 26 experiences a combined vertical and torsional vibration the vertical and torsional modes of which may be controlled separately.

The DASP incubation module 26 comprises a single spiral having a clockwise track 50 leading from its circumference towards its centre. This module 26 acts as a holding zone in which the DASP reacts with the anti-body-antigen bound fraction and advantageously the vibratory motion is employed to agitate the solutions maintaining the solid phase material in suspension, in addition to propelling the sample containers 31 around the track 50. Agitation is conveniently achieved by separating the horizontal and vertical components of the vibratory force and varying the amplitude of the vertical component in a controlled fashion in conjunction with the use of a rubber ridged floor on the spiral track. Lower amplitude vibrations of the vertical component cause the sample container 31 to bump against the ridges and hence agitate the liquid contents, whereas high amplitude vibrations cause the sample containers 31 to surmount the ridges and continue their desired forward migration. Various arrangements may be used for separating the vertical and horizontal components of the vibration, and the solution proposed by Redford (U.K. Pat. No. 1,154,042) is particularly preferred.

It has been found that the vibration system used in the standard modules has no effect on the settling of the DASP through the sucrose, and it is therefore possible to feed the tubes 31 directly from the DASP module 26 into a spiral settling module 27. Since the DASP agitation times and the settling times are short, only single spirals are required for these modules 26 and 27, the time delays between the additions of DASP at geneva 51 and the 10% sucrose at geneva 53 being 30 minutes, delay between 10% sucrose extraction and 20% sucrose additions, both at geneva 54, −10 mins. and between 20% sucrose addition and its extraction at geneva 55,− 10 mins. The tubes 31 then arrive at geneva gate mechanisms 56 and 57 at which they are held for counting; small well-type γ-detectors 58 and 59 e.g. of the kind produced by MINI Instruments Ltd, rise from below to enclose the sample tubes 31 for the required counting period e.g. 15 seconds.

Two or more detectors may be used in series, as described above, so as to increase the sample throughput, in which case it may be necessary to increase the storage capacity of the system, although this modification may be used under normal conditions to allow for increased counting times whilst maintaining a fast rate of sample throughput during the earlier stages of the assay.

A bar code reader e.g. a fibre optics pen (not shown) is conveniently situated immediately above the counter well, and attached to the counter body so that as the body of the counter is raised to enclose the tube in the well, the reader automatically reads the patient information which in an automated system is then printed out alongside with the value of the count and the concentration of antigen as measured and calculated by suitable computing equipment.

Figure 5:
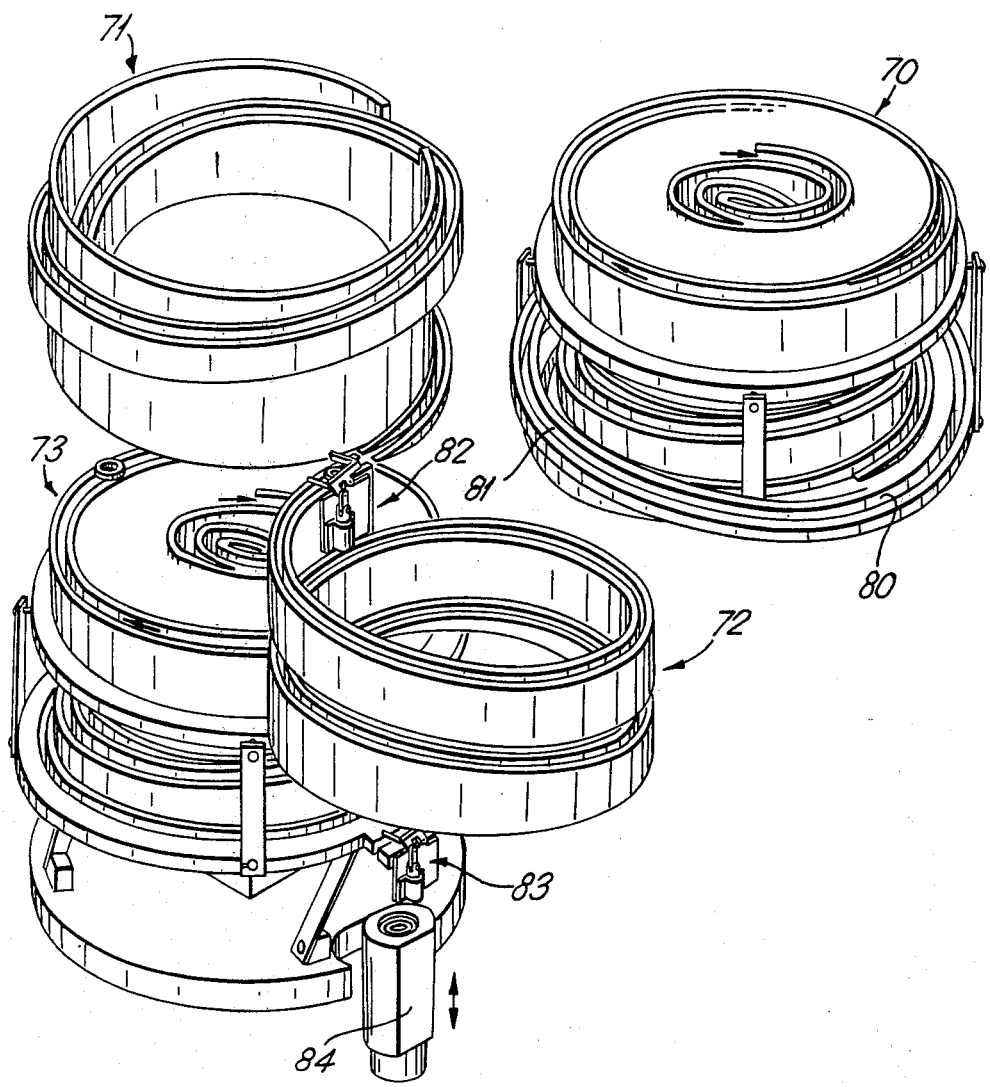
FIG. 5 is a view of a completely automatic RIA system for assays employing solid phase first antibody.
Figure 8:
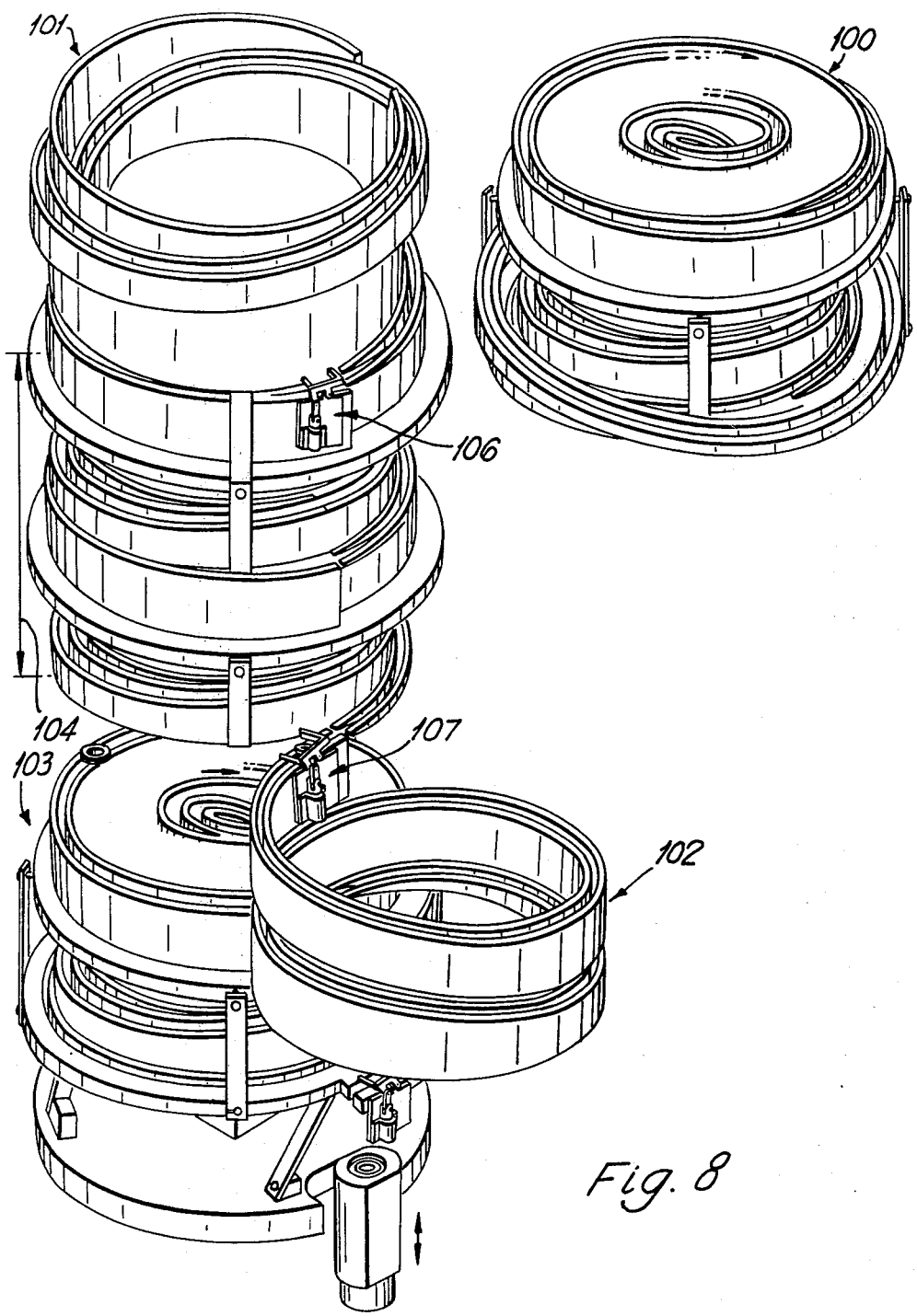
FIG. 8 is a view of a completely automatic RIA system for assays employing solid phase second antibody (DASP) separation.

Alternative arrangements for completely automatic RIA systems are shown in FIGS. 5 and 8, based on stacks of interconnecting spiral units.

FIG. 5 represents a completely automated RIA system for assays using the solid-phase first antibody technique, and is modular in construction consisting of a sample store module 70, a vibratory bowl feeder 71, an agitator module 72 and a combined separator and counter module 73. The sample store module 70 is of the usual double spiral type as described previously with reference to FIGS. 1 and 2, though with the modification that the output end of the vibratory track 80 at the periphery of the lower spiral is connected by a helical track 81 rising around the outside of the module to the input at the periphery of the upper spiral thus providing a closed loop circuit. Containers of samples e.g. serum, plasma or urine samples, will continue to circulate round the closed loop whilst vibratory force is applied to the module and gate mechanisms (not shown) are operated. The vibratory bowl feeder module 71 is substantially as the corresponding module described previously with reference to FIG. 3, feeding empty sample containers into the system. Aliquots of same liquids are transferred from tubes in module 70 to empty tubes supplied from module 71 and reagents are added to these latter tubes at appropriate gated stations. Lever gate mechanism 82 is located downstream of module 71 providing a station for addition of labelled antigen (*Ag) and solid-phase first antibody to the sample tubes. From here the sample tubes pass into the agitator module 72 which is located to one side out of the main stack of modules 71 and 73, and is in the form of a two circuit helix. The mode of operation and vibration of agitator module 72 is substantially as previously described for module 26 of FIG. 3. From agitator module 72 the sample tubes pass to the combined separation and radioactive counting module 73 which is in the customary, double spiral form to provide an enlarged queuing zone prior to counting. At a convenient point, usually towards the periphery of the lower spiral, sucrose solution is added to the containers in turn to effect separation of the solid phase antibody reagent from suspension by the method of our copending U.K. patent application No. 47078/75. Thereafter supernatant liquid may be removed, though this may not be necessary, and the containers are counted, the containers being held at lever gate mechanism 83 and the well type γ-counter 84 rising from below to enclose the sample container for the requisite counting period. Information relating to the count and sample origin are read and recorded as previously described.

Figure 6:
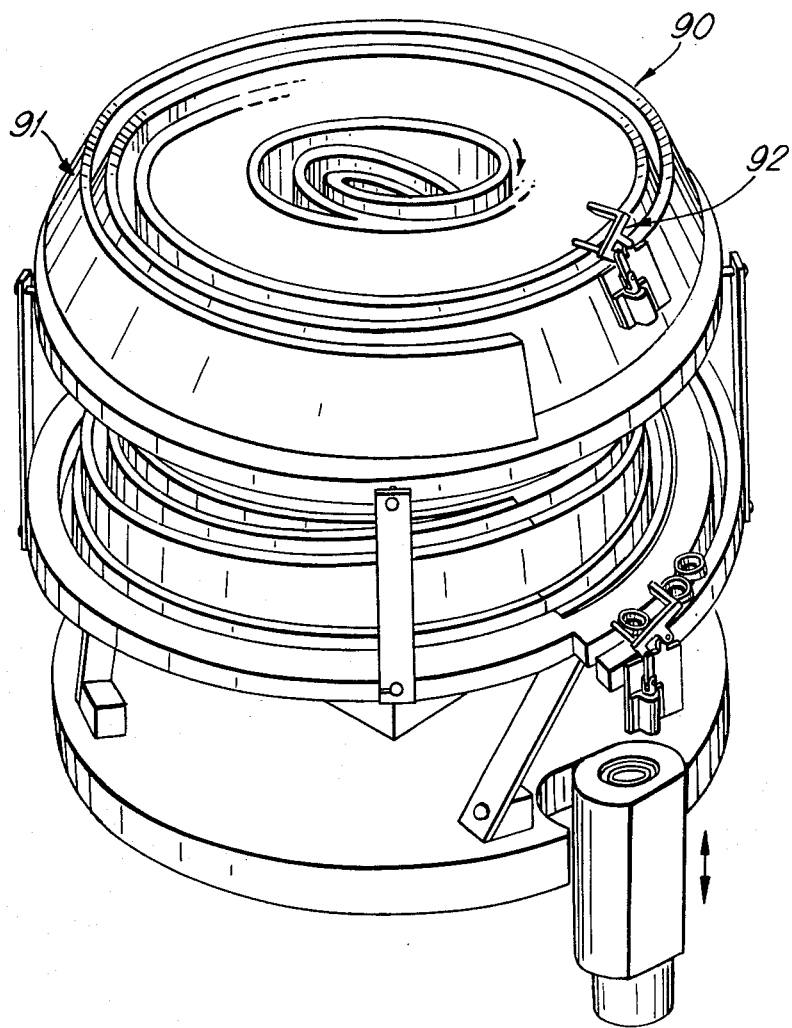
FIG. 6 is a view of an alternative preferred combined agitator-separator-counter module for use in the apparatus of FIG. 5 and similar systems.

With reference to FIG. 6 a preferred modification for use in the apparatus of FIG. 5 or FIG. 7 (as hereinafter described) comprises a combined agitator-separator-counter module. The module shown in FIG. 6 is similar in construction and operation to the module 73 comprising the basic double spiral unit, though modified at the periphery of the upper spiral 90. The outer circuit 91 of the upper spiral 90 is tilted inwards at an angle of elevation of about 40° from the horizontal so that sample containers within this circuit rest on their sides with their tops leaning towards the centre of the spiral. Towards the inner end of this section of inclined track 91 a lever gate mechanism 92 is provided to hold up the tubes in a queue within the inclined section 91. The vibratory motion acting on the queued tubes causes them to undergo a gentle turning over motion which mixes their contents. After the desired period of agitation the gate mechanism 92 operates to release each tube in turn to pass on round the double spiral for separation and counting. This modification dispenses with the requirement for a separate agitator module and permits the combination of modules in a single stack.

Figure 7:
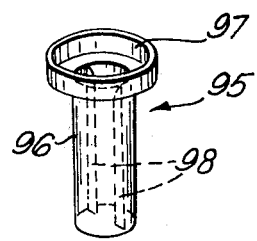
FIG. 7 is a view of a preferred sample container suitable for use in the apparatus of FIG. 6.

With reference to FIG. 7 the mixing effect of the agitator may be enhanced by use of specially modified sample tubes. These tubes 95 are in the usual overall form having a tubular lower section 96 to contain the sample and an upper enlarged collar section 97 to rest on the upper surface of the vibratory track, and is modified by inclusion of two elongate webs or baffles 98 lying facing one another down the internal walls of the tubular section 96. Without these baffles 98, however, mixing achieved with the modified mixer of FIG. 6 is still highly satisfactory.

With reference to FIG. 8, RIA systems employing DASP separation may be modified in the form of a stack of double spiral modules as for the apparatus of FIG. 5. The apparatus of FIG. 8 is similar to the solid phase first antibody apparatus described above comprising sample store 100, vibratory bowl feeder 101, agitator 102 and combined separation and counting 103 modules. In addition, the DASP assay apparatus includes an incubation module 104 between the vibratory bowl feeder 101 and the agitator 102 consisting of two linked double spirals and providing holding zones for incubation of sample with first antibody (Ab) and labelled antigen (*Ag). At the exit of the feeder module 101 is gate 106 at which tubes are arrested for addition of first antibody (Ab), and from where the tubes pass into the first double spiral of module 104 where the first incubation takes place. At the centre of the second double spiral of module 104 is a second gate mechanism (not shown) for addition of *Ag to the tubes and from where tubes pass into the remainder of module 104 and undergo the second incubation. At the exit of module 104 is further gate mechanism 107 serving to queue tubes in module 104 and also act as a station for addition of solid-phase second antibody (DASP) to the tubes. From here the tubes pass on into the agitator 102 and combined separator and counting 103 modules and are processed as described previously. The agitator module 102 may advantageously be combined with the separator-counter module 103 as described previously with reference to FIG. 6.

Figure 9:
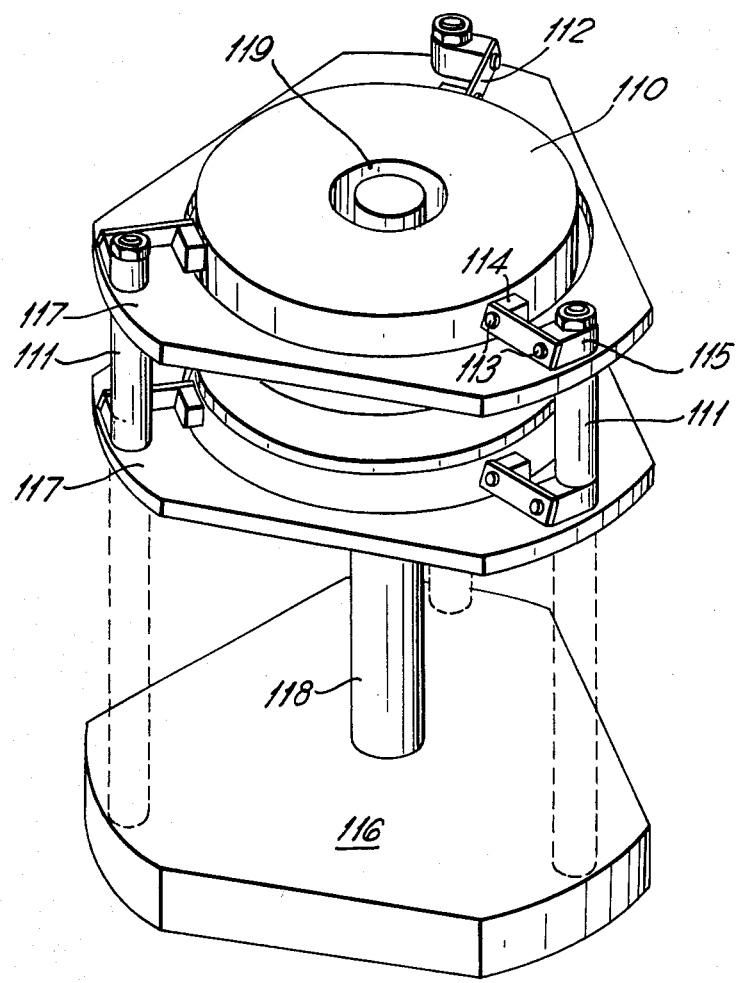
FIG. 9 is a part view of a preferred arrangement of an interconnected stack of spiral units.

The linked stacks of spiral units of FIGS. 5 and 8 are shown with a single vibratory drive at the base of the separator-counter module 73 or 103 which may in some cases be used to drive the complete stack of spirals which are rigidly connected to the base spiral. Preferably, however, each spiral is supplied with a separate vibratory drive and each spiral is independently freely mounted to a rigid framework connected to a firm solid base. One solution is given by the structure shown diagrammatically in FIG. 9 in which a circular spiral unit 110 is mounted on three triangularly spaced rigid vertical pillars 111 by resilient leaf springs 112 held by screws 113 to blocks 114 and 115 which in turn are connected to the spiral unit 110 and pillars 111 respectively. The lower ends of the pillars 111 are held firmly in a heavy solid base plate 116, and their upper ends are held rigidly in their triangularly spaced arrangement by triangular plates 117 disposed at intervals along the lengths of the pillars 111. The spiral units 110 are thereby supported and are free to oscillate torsionally about a vertical axis, passing through their centres, against leaf springs 112.

Each spiral unit 110 is supplied independently with a vibratory drive. In one arrangement a vertical pillar 118 passing up through circular holes 119 at the centre of the spiral units 110 carries electromagnetic coils (not shown) at intervals along its length corresponding to spiral units 110. The spiral units 110 are provided with permanent magnet collars (not shown) which interact with the electromagnetic coils when they are energised with an alternating electric current to cause the spiral units to undergo torsional oscillations about the axis of pillar 118. Alternatively the oscillatory motion is provided by piezoelectric crystals attached to the leaf springs 112.

Figure 10:
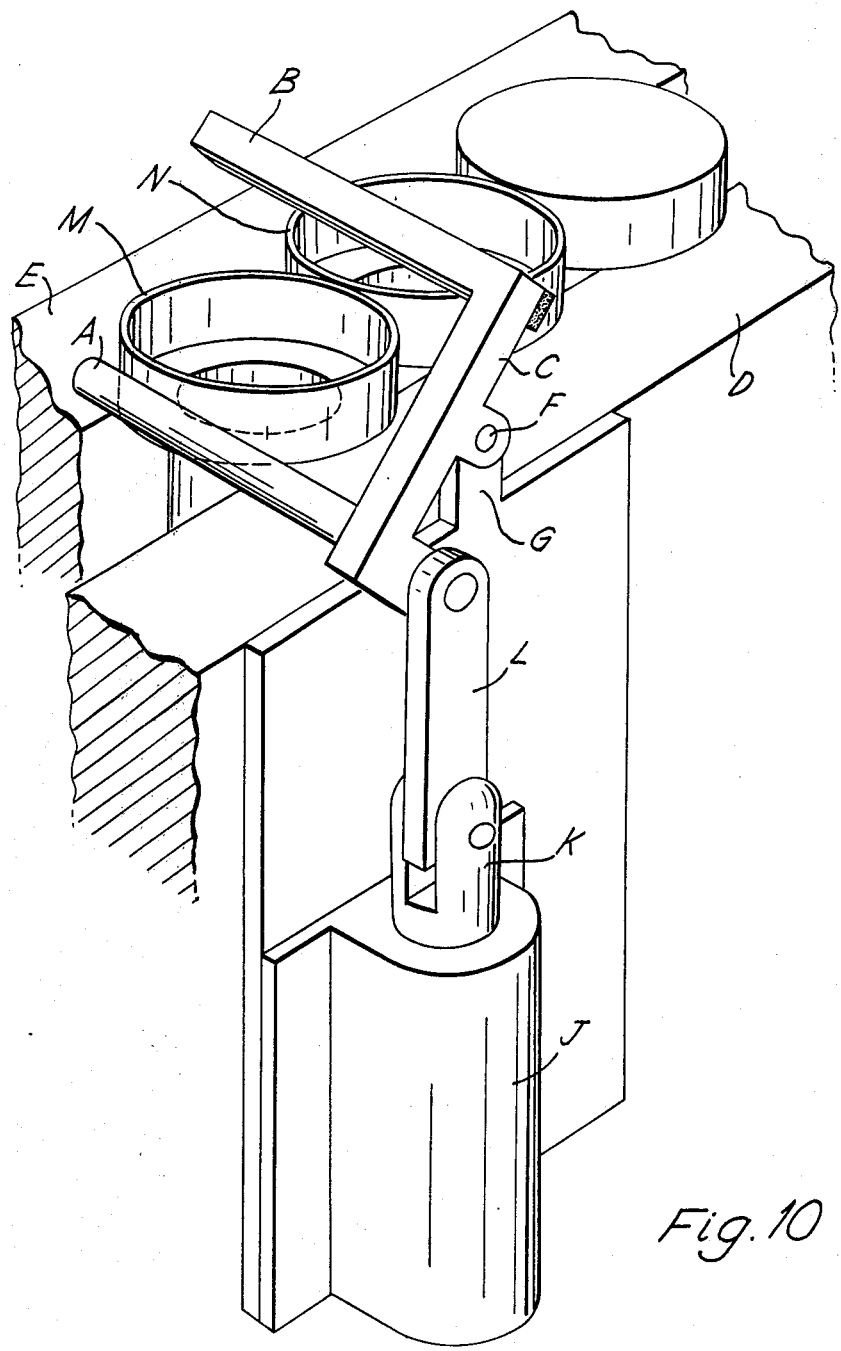
FIG. 10 is a close-up view of a length of vibratory track equipped with a preferred lever gate mechanism.

Preferred level type gate mechanisms are employed to arrest the passage of sample tubes throughout the systems of FIGS. 5, 6 and 8, and, with reference to FIG. 10, one such mechanism is now described by way of illustration. The mechanism comprises combined barrier and clamping means actuated by a solenoid or piston device. The gate mechanism comprises parallel elongate barrier A and clamping B members joined at one end by interconnecting member C. The barrier A and clamping B members are disposed across a length of vibratory conveyor track D and E, and the interconnecting member is pivoted on pin F at its mid point about an axis perpendicular to its length. The pin F is located in a tab G extending from the top edge of plate H attached to the outer side face of member D of the vibratory track. The gate mechanism is activated by a gas driven cylinder or electrically operated solenoid J attached to plate H. The cylinder or solenoid act to advance or withdraw a shackle shaped piece K pivotally connected to connecting plate L which in turn is pivotally connected to the barrier member A end of interconnecting member C.

In the normal rest position, shown in FIG. 10, the barrier member A lies across the vibratory track D and E hindering the passage of sample tube M and causing a queue to form. When cylinder or solenoid J is activated piece K is advanced causing member C to pivot about pin F. The barrier member A is raised releasing the first sample tube which proceeds on through the system, whilst the clamping member B lowers onto the second sample tube N clamping it in position. On return to the normal rest position piece K retreats lowering barrier A and raising clamping member B permitting the quene to advance by one sample tube.

We claim:

1. A method of conveying samples in a discrete sample analysis apparatus wherein at least one discrete test sample is placed in at least one sample container, comprising:

supporting the at least one sample container on a conveyor track; and, vibrating the conveyor tracks such that the sample container is conveyed along the track.

2. An automated discrete analysis system wherein at least one discrete test sample is placed in at least one sample container and transported to predetermined locations for subjection to analytical procedures comprising:

a conveyor track on which said sample container is supported; and, means for vibrating said conveyor track such that said sample container travels along said track to said predetermined locations;

whereby the vibration of said track propells said container therealong.

3. A system according to claim 2, for automation of a binding assay or immunometric assay technique.

4. A system according to claim 2, for automation of a radio-immunoassay technique.

5. A system according to claim 2, wherein said conveyor track comprises:

pairs of spaced apart parallel elongate members between which said sample containers hang freely supported by the members.

6. A system according to claim 2, in which the conveyor is vibrated either electromagnetically or piezoelectrically.

7. A system according to claim 2, further comprising: a vibratory bowl feeder for feeding sample containers into the system.

8. A system according to claim 2, further comprising one or more gate mechanisms at appropriate points along the conveyor track to arrest sample containers to allow for time lapses required by the system analysis.

9. A system according to claim 8, in which said one or more gate mechanisms comprises:

lever type gate mechanisms comprising combined barrier and clamping means, which either bar passage to sample containers causing a queue to form, or, on actuation, act to release the first one or more containers to proceed along the conveyor whilst clamping the second or a subsequent container to maintain the queue.

10. A system according to claim 2, in which said conveyor track comprises:

a spiral type conveyor track providing a queuing zone for said sample containers.

11. A system according to claim 10, in which a plurality of linked spirals are employed.

12. A system according to claim 10, further comprising:

a plurality of linked spirals stacked one on top of the other with adjacent spirals mutually reversed.

13. A system according to claim 3, for automation of a binding assay in which solid phase first antibody or solid phase second antibody techniques are employed to separate bound and free labelled antigen.

14. A system according to claim 2, in which the vibratory motion of the conveyor is used to agitate solution and/or hold solid phase material in suspension during incubation.

15. A system according to claim 2, wherein said conveyor track has a ridged floor, and said means for supplying vibratory motion to the conveyor generates a vertical vibration component which is varied such that low amplitude vibration vibrates the sample containers against the ridges and agitates the solutions, and high amplitude causes the containers to surmount the ridges and so progress along the conveyor track.

16. A system according to claim 2, further comprising:

said vibratory track inclined transversely in relation to its length such that sample containers maintained in the track rest on their sides at an angle out of the vertical;

the track provided with gate mechanisms such that sample containers form a queue resting on their sides within the conveyor track; and said means for applying a vibratory motion to the track disposed such that sample containers execute a gentle rolling motion and thereby mix their contents.

17. A system according to claim 16, in which the track is inclined such that sample containers maintained in the track rest at an angle of elevation of up to 50° from the horizontal.

18. A system according to claim 2, comprising:

a separation module for separating solid and liquid components of mixtures; and, the conveyor track having a gated station for addition of a second liquid having a density intermediate between those of the solid and liquid components of the mixture.

19. A system according to claim 2, further comprising:

a counter-detector; and the conveyor track having a gated station towards the exit end thereof for interaction with the detector.

20. A system according to claim 2, further comprising:

the conveyor track having a gated sampling station and means for transferring aliquots of sample from sample tubes held at the gated sampling station.

21. A system according to claim 12, in which the spiral units of the stack are vibrated independently and each is located freely by resilient mountings within a rigid framework.

22. A system according to claim 2, further comprising:

a gate mechanism comprising a lever mechanism providing combined barrier and clamping means which act either to bar passage of a queue of sample containers, or, on actuation, to clamp the second or subsequent container of the queue whilst releasing the first container or containers to proceed along the conveyor track.

23. A system according to claim 15, in which the sample container includes one or more webs or baffles down the internal surface of the container walls such that the container can be used as an agitator module.

* * * * *